United States Patent [19]
Klemann et al.

[11] Patent Number: 5,219,605
[45] Date of Patent: Jun. 15, 1993

[54] SILOXY ESTER DERIVATIVES AS LOW CALORIE FAT MIMETICS

[75] Inventors: Lawrence P. Klemann, Somerville; John W. Finley, Whippany, both of N.J.

[73] Assignee: Nabisco, Inc., Parsippany, N.J.

[21] Appl. No.: 781,438

[22] Filed: Oct. 23, 1991

Related U.S. Application Data

[63] Continuation-in-part of Ser. No. 527,066, May 21, 1990, Pat. No. 5,124,166, and a continuation-in-part of Ser. No. 439,103, Nov. 20, 1989, which is a continuation-in-part of Ser. No. 231,393, Aug. 12, 1988, abandoned, which is a continuation-in-part of Ser. No. 85,434, Aug. 13, 1987, Pat. No. 4,830,787.

[51] Int. Cl.$^5$ ............................................... A23L 1/29
[52] U.S. Cl. ................................. 426/531; 426/611; 426/804
[58] Field of Search ..................... 426/531, 611, 804; 556/400, 445

[56] References Cited

U.S. PATENT DOCUMENTS

| | | |
|---|---|---|
| 519,980 | 5/1894 | Winter . |
| 2,962,419 | 11/1960 | Minich . |
| 3,495,010 | 2/1970 | Fossel . |
| 3,600,186 | 8/1971 | Mattson et al. . |
| 3,637,774 | 1/1972 | Babayan . |
| 3,876,794 | 4/1975 | Rennhard . |
| 4,005,195 | 1/1977 | Jandacek . |
| 4,304,768 | 12/1981 | Staub . |
| 4,508,746 | 4/1985 | Hamm . |
| 4,582,927 | 4/1986 | Fulcher . |
| 4,734,287 | 3/1988 | Singer . |
| 4,797,300 | 1/1989 | Jandacek . |
| 4,840,815 | 6/1989 | Meyer . |
| 4,849,242 | 7/1989 | Kershner . |
| 4,855,156 | 8/1989 | Singer et al. . |
| 4,861,613 | 8/1989 | White et al. . |
| 4,911,946 | 3/1990 | Singer . |
| 4,915,974 | 4/1990 | D'Amelia . |
| 4,925,692 | 5/1990 | Ryan . |
| 4,980,191 | 12/1990 | Christensen . |

FOREIGN PATENT DOCUMENTS

| | | |
|---|---|---|
| 1106681 | 11/1978 | Canada . |
| 205273 | 12/1986 | European Pat. Off. . |
| 233856 | 8/1987 | European Pat. Off. . |
| 236288 | 9/1987 | European Pat. Off. . |
| 375031 | 6/1990 | European Pat. Off. . |

OTHER PUBLICATIONS

Chemical Abstracts 113(5):331192 1990.
Chemical Abstracts 108(11):91336 1987.
STN Database, Registry File, RN 127052-99-7, 1992.
STN Database, Registry File, RN 112904-68-4, 1992.
Booth, A. N. and Gros, A. T., 40 J. Amer. Oil Chem. Soc. 551-2 (1963).
Bracco, E. F., et al., 46 Am. J. Clin. Nutr. 784-789 (1987).
Goodman and Gilman's Pharmacological Basis of Therapeutics, 7th ed., Macmillan Publ. Co., N.Y. 1985, pp. 1002-1003.
Gottenbos, J. J., chapter 8 in Beare-Rogers, J., ed., Dietary Fat Requirements in Health and Development, A.O.C.S. 1988, p. 109.
Hamm, D. J., 49 J. Food Sci. 419 (1984).
Hashim, S. A., and Babayan, V. K., 31 Am. J. Clin. Nutr. S273-276 (1978).
Haumann, B. J., 63 J. Mer. Oil Chem. Soc. 278 (1986).
LaBarge, R. G. 42 Food Tech. 84 (1988).
Mead, J., et al., Lipids, Plenum, N.Y., 1986, p. 459.
Stryker, W. A., 31 Arch Path. 670 (1941).

*Primary Examiner*—Joseph Golian
*Assistant Examiner*—Evan Federman

[57] ABSTRACT

Siloxy ester derivatives, notably compounds having a two-to twelve-carbon backbone to which is attached one to five fatty groups in ester or reversed ester linkage, and one or two siloxy groups each bearing three pendant aliphatic, ether, or ester groups, comprise a new class of edible fat mimetics. These compounds have the general formula

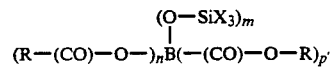

where B is an aliphatic group having 2 to 12 carbons, X is an alkyl or oxaalkyl having 1 to 18 carbons (or mixtures thereof), or an ester group of the formula —O—(-CO)—R, R is an aliphatic group having 1 to 29 carbons, m is 1 or 2, and n+p is 1 to 5. Methods of using the new fat mimetics and food compositions incorporating them are disclosed.

26 Claims, No Drawings

SILOXY ESTER DERIVATIVES AS LOW CALORIE FAT MIMETICS

RELATED APPLICATIONS

This application is a continuation-in-part of copending application Ser. No. 07/527,066, now U.S. Pat. No. 5,124,166, filed May 21, 1990, and application Ser. No. 07/439,103, filed Nov. 20, 1989, which were continuations-in-part of Ser. No. 07/231,393, filed Aug. 12, 1988, now abandoned, which, in turn, was a continuation-in-part of Ser. No. 07/085,434, filed Aug. 13, 1987, now U.S. Pat. No. 4,830,787.

BACKGROUND OF THE INVENTION

This invention relates to the use of siloxy ester derivatives, notably compounds having a two- to twelve-carbon backbone to which is attached one to five fatty groups in ester or reversed ester linkage and one or two siloxy groups as edible fat mimetics.

Dietary fat is the most concentrated source of energy of all the nutrients, supplying 9 kcal/gram, about double that contributed by either carbohydrate or protein. The amount of fat in the American diet has increased in the last 60 years by about 25% (Mead, J., et al. Lipids, Plenum, N.Y., 1986, page 459), so that fats now provide approximately 40% (or more) of the daily caloric intake. Moreover, technological advances in the food industry, including efficient and safe hydrogenation procedures, have changed the kind of fat in foods.

Because fats are high in calories and because certain fats appear to pose a health risk when consumed in large quantities over time, a number of national advisory committees on nutrition have made recommendations differing in detail, but the common theme is a reduction in the total amount of fat in the diet (Gottenbos, J.J., chapter 8 in Beare-Rogers, J., ed., Dietary Fat Requirements in Health and Development, A.O.C.S. 1988, page 109). Yet fat contributes to the palatability and flavor of food, since most food flavors are fat-soluble, and to the satiety value, since fatty foods remain in the stomach for longer periods of time than do foods containing protein and carbohydrate. Furthermore, fat is a carrier of the fat-soluble vitamins, A, D, E, and K, and the essential fatty acids, which have been shown to be important in growth and in the maintenance of many body functions. Hence, major research efforts have focused on ways to produce food substances that provide the same functional and organoleptic properties as fats, but not the calories.

A number of fat replacements have heretofore been suggested (recently reviewed by Hamm, D.J., 49 J. Food Sci. 419 (1984), Haumann, B.J., 63 J. Amer. Oil Chem. Soc. 278 (1986) and LaBarge, R.G., 42 Food Tech. 84 (1988)). Hamm divides replacement fats into two broad categories: structurally reengineered triglycerides modified to retain their conventional functional properties in foods, while removing their susceptibility toward hydrolysis or subsequent absorption during digestion, and materials developed from chemistry unrelated to triglycerides yet having physical properties similar to edible fats.

Examples of the former class of triglyceride analogues include compounds having the glycerol moiety replaced with alternate polyols (e.g., pentaerythritol in U.S. Pat. No. 2,962,419 to Minich, or sugars in U.S. Pat. No. 3,600,186 to Mattson and Volpenhein and U.S. Pat. No. 4,840,815 to Meyer, et al.); compounds having the fatty acids replaced with alternate acids (e.g., branched esters as described in U.S. Pat. No. 3,579,548 to Whyte); compounds having insertions between the glycerol and the fatty acid (e.g., ethoxy or propoxy groups in U.S. Pat. No. 4,861,613 to White and Pollard); compounds having reversed esters (e.g., malonates in U.S. Pat. No. 4,582,927 to Fulcher, trialkoxytricarballylates in U.S. Pat. No. 4,508,746 to Hamm); and compounds having the ester bonds replaced by ether bonds (Can. Pat. No. 1,106,681 to Trost).

Examples of the latter category of fat replacements chemically unrelated to triglycerides are mineral oil (suggested as early as 1894 in U.S. Pat. No. 519,980 to Winter); polyglucose and polymaltose (U.S. Pat. No. 3,876,794 to Rennhard); jojoba wax (W. Ger. Pat. No. 3,529,564 to Anika); polyoxyalkylene esters (U.S. Pat. No. 4,849,242 to Kershner), polyvinyl alcohol esters (U.S. Pat. No. 4,915,974), and polymerized $C_{18}$ fatty acid ethyl esters (U.S. Pat. No. 4,980,191 to Christensen). Polysiloxanes, have a linear polymeric structure consisting of the generic formula,

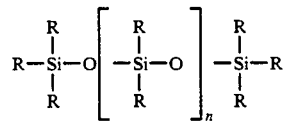

where the R groups are methyl or methyl and phenyl or the like groups, have also been identified (Bracco, E.F., et al. 46 Am. J. Clin. Nutr. 784–789 (1987) and Eur. Pat. Ap. No. 205,273 to Frye).

Nondigestible or nonabsorbable edible fat replacements have proved disappointing when tested in feeding trials, where gastrointestinal side effects occurred, in some cases so extreme that frank anal leakage was observed. Nondigestible fats appear to act as a laxative and are expelled from the body, eliciting foreign body reactions like those early documented for mineral oil (Stryker, W.A., 31 Arch. Path. 670 (1941), more recently summarized in Goodman and Gilman's Pharmacological Basis of Therapeutics, 7th ed., Macmillan Pub. Co., N.Y. 1985, pp. 1002–1003). In the U.S.D.A.'s assessment of the caloric availability and digestibility of a series of new-type fats in the 1960's (e.g., amylose fatty acid esters, diglyceride esters of succinic, fumaric, and adipic acids, and polymeric fats from stearic, oleic and short-chain dibasic acids; see Booth, A.N., and Gros, A.T., 40 J. Amer. Oil Chem. Soc. 551 (1963)), for example, rats fed the experimental fats exhibited undesirable gastrointestinal side effects similar to what had already been observed with mineral oil consumption by people. In several of the balance studies, the diarrhea was so extreme that digestibility coefficients could not be calculated in the trial feedings (ibid., Table I, p. 552). Polyglycerol and polyglycerol esters, suggested as fat replacements by Babayan and Lehman (U.S. Pat. No. 3,637,774), have been suggested for use as fecal softening agents as well (U.S. Pat. No. 3,495,010 to Fossel).

A number of remedies have been recommended to combat the anal leakage observed when sucrose polyesters are ingested (e.g., employing cocoa butters, U.S. Pat. No. 4,005,195 to Jandacek, incorporating saturated fatty groups, Eur. Pat. Ap. Pub. No. 233,856 to Bernhardt, or mixing residues, U.S. Pat. No. 4,797,300 to Jandacek, et al.), and dietary fiber preparations have been incorporated into polysaccharide and/or polyolcontaining foodstuffs to help inhibit the diarrheal effect (U.S. Pat. No. 4,304,768 to Staub et al. and Eur. Pat. Ap. Pub. No. 375,031 to DeBoer and Kivits). Saturated fatty acids have been disclosed as anti-anal leakage agents for polyorganosiloxane fat substitutes (U.S. Pat. No. 4,925,692 to Ryan), and dietary fiber preparations have been incorporated into foodstuffs containing other fat replacements to help inhibit the diarrheal effect (U.S. Pat. No. 4,304,768 to Staub et al. and Eur. Pat. Ap. No. 375,031 to DeBoer and Kivits).

SUMMARY OF THE INVENTION

An object of the present invention is to provide a unique approach to the structuring of edible fat mimetic compounds. More particularly, it is an object of the present invention to provide a new group of edible fat replacement compounds combining some of the features of triglyceride analogues with compounds chemically different from triglycerides. It is a further object of the present invention to suggest fat mimetic compounds which can have functional groups tailored to modulate caloric availability, while minimizing laxative side effects.

These and other objects are accomplished by the present invention, which describes siloxy ester derivatives, a new class of edible synthetic fat mimetics, methods of using them, and food compositions incorporating them. These compounds have a two- to twelve-carbon aliphatic backbone to which is attached one to five fatty groups in ester or reversed ester linkage and one or two siloxy groups, each bearing three pendant aliphatic, ether, or ester groups as edible fat mimetics. These compounds have the general formula

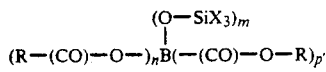

where
B is an aliphatic group having 2 to 12 carbons,
X is an alkyl or oxaalkyl having 1 to 18 carbons (or mixtures thereof), or an ester group of the formula —O—(CO)—R,
each R is, independently, an aliphatic group having 1 to 29 carbons,
m = 1 or 2,
n = 0 to 5, and
p = 0 to 5,
provided that n + p = 1 to 5.
In preferred compounds, B has 3 to 6 carbons and m + n + p = 3 or 4.

DETAILED DESCRIPTION OF THE INVENTION

The compounds of this invention, herein referred to as siloxy ester derivatives, have a two- to twelve-carbon backbone to which is attached one to five fatty groups in ester or reversed ester linkage and one or two siloxy groups, each bearing three aliphatic, ether, or ester groups as edible fat mimetics. These compounds have the general formula

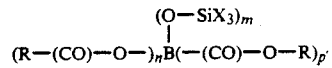

where
B is an aliphatic group having 2 to 12 carbons,
X is an alkyl or oxaalkyl having 1 to 18 carbons (or mixtures thereof), or an ester group of the formula —O—(CO)—R,
each R is, independently, an aliphatic group having 1 to 29 carbons,
m, n and p are integers,
m = 1 or 2,
n = 0 to 5, and
p = 0 to 5,
provided that n + p = 1 to 5.
In preferred compounds, B has 3 to 6 carbons and m + n + p = 3 or 4. The invention resides not only in the edible compositions, but also in the novelty of fatty siloxy esters.

The compounds of this invention include siloxy carboxylate ester compounds of the formula

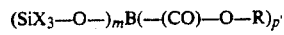

where B, X, m and p are as defined above. In preferred members of this group, B has 3 to 6 carbons and m + p = 3 or 4. One embodiment has m = 1 and p = 2. Another embodiment has m = 2 and p = 1. The latter includes compounds of the formula

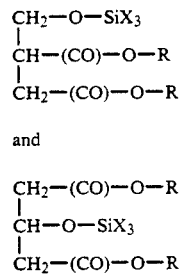

where
X is an alkyl or an oxaalkyl having 1 to 18 carbons, or ester group of the formula —O—(CO)—R,
and R is an aliphatic group having 1 to 29 carbons.
The compounds of this invention also include siloxy ester compounds of the formula

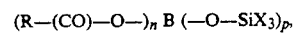

where B, X, n and p are as defined above. In preferred members of this group, B has 3 to 6 carbons and n + p = 3 or 4. One embodiment has n = 1 and p = 2. Another embodiment has n = 2 and p = 1. The latter includes compounds of the formula

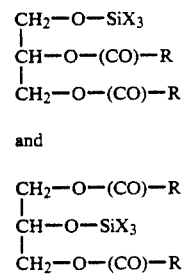

where
X is an alkyl or an oxaalkyl having 1 to 18 carbons; or ester group of the formula —O—(CO)—R,
and R is an aliphatic group having 1 to 29 carbons.

Siloxy esters have a backbone, B, which is an aliphatic group having 2 to 12 carbons. By "backbone" is meant a group that serves as a point of attachment for pendant siloxy groups (—O—SiX$_3$), pendant carboxy ester groups (—O—(CO)—R), and pendant carboxylate (reversed ester) groups (—(CO)—O—R). The pendant ester groups are analogous to the ester residues found in natural triglycerides (having the ester oxygen covalently bonded to the backbone), while the reversed ester have a configuration which is reversed compared to natural triglycerides (and have a carboxylate carbon covalently bonded to the backbone).

The compounds of this invention may be envisioned as being derived from alcohols or hydroxycarboxylic acids derivatized with one or two siloxy groups and esterified and/or acylated with fatty acids or fatty alcohols or their derivatives. Using this analogy, in preferred compounds having a 3- to 6-carbon backbone bearing three pendant groups (m+n+p) can be envisioned as derived from linear or branched, saturated or unsaturated alcohols such as, for example, glycerol, tris-hydroxymethyl ethane, trishydroxymethyl propane, butane-triol, pentanetriol, hexanetriol, and so forth, or from linear or branched, saturated or unsaturated hydroxycarboxylic acids such as, for example, malic, citramalic, hydroxyglutaric, hydroxyadipic, hydroxyhexanedioic, hydroxyheptanedioic, dihydroxypropanoic, dihydroxybutanoic, dihydroxypentanoic, hydroxymethyl malonic, and the like. As used herein, chemical names (and formulae) include isomeric variations.

Siloxy esters have at least one ester group attached to backbone B. These include 0 to 5 (n) ester (carboxy) groups, —O—(CO)—R, and 0 to 5 (p) reversed ester (carboxylate) groups (—(CO)—O—R). The sum of the ester and reversed ester groups varies from 1 to 5, preferably 3 to 4. Ester groups are derived by acylating an hydroxyl, —OH, with a fatty acid of the formula RCOOH or a fatty acid derivative, wherein each R is, independently, a straight or branched, saturated or unsaturated aliphatic group having 1 to 29 carbons. Examples of fatty acids include, but are not limited to, acetic, propionic, butyric, caproic, caprylic, pelargonic, capric, undecanoic, lauric, myristic, palmitic, stearic, arachidic, behenic, lignoceric, cerotic, montanic, melissic, palmitoleic, oleic, erucic, brassisdic, vaccenic, linoleic, linolenic, eleostearic, arachidonic, nervonic, eicosapentaenoic, docosatetraenoic, docosapentaenoic, docosahexaenoic, and the like acids.

The reversed ester groups are derived by esterifying a carboxylate group, —COOH, with a fatty alcohol of the formula RCH$_2$OH, where R is as defined above. Preferred fatty alcohols include acetyl, ethyl, propyl, butyl, hexyl, caprylyl, pelargonyl, capryl, lauryl, undecanyl, myristyl, palmityl, stearyl, arachidyl, behenyl, lignoceryl, cerotyl, montanyl, melissyl, palmitoleyl, oleyl, vaccenyl, linoleyl, linolenyl, eleostearyl, arachidyl, nervonyl, eicosapaentanyl, docosatetraenoyl, docosapentaenyl, docosahexaenyl, and the like alcohols.

Mixtures of fatty acids and alcohols may also be used, such as those obtained from non-hydrogenated, partially hydrogenated or fully hydrogenated soybean, safflower, sunflower, high oleic sunflower, sesame, peanut, corn, olive, rice bran, canola, babassu nut, coconut, palm, palm kernel, lupin, nasturtium seed, mustard seed, cottonseed, low erucic rapeseed, high erucic rapeseed, meadowfoam or marine oils, fats such as shea or dairy butter, lard or tallow, or plant waxes such as jojoba. Specific fractions of natural or processed oils, fats or waxes may also be used.

All siloxy esters have at least one and as many as two siloxy groups. By "siloxy group" is meant a group of the formula —O—SiX$_3$, where X is an alkyl or oxaalkyl having 1 to 18 carbons, or mixtures thereof, or an ester group. When X is an alkyl, it has the formula —(CH$_2$)$_q$CH$_3$, with m=0 to 18. When X is oxaalkyl, it has the formula —O—(CH$_2$)$_q$—CH$_3$, with q=0 to 19. When X is an ester group, it has the formula —O—(-CO)—R, wherein R is as defined above.

The R and X groups will be selected to provide a discernible fatty character in the compounds. Thus, typically, most of the R groups have 2 to 4 or more carbon atoms, with ≧75% containing 3 to 23 (derived from acids having 4 to 24 carbons), more narrowly 9 to 19, and even more narrowly, 15 to 17 carbon atoms. Preferred fat mimetics can have an array of R groups selected to include 95% having 13 to 17 carbon atoms. In one embodiment, two of the R groups should be predominantly saturated C$_{13}$ to C$_{17}$ groups. In another embodiment, two of the R groups should be predominantly unsaturated C$_{15}$ to C$_{17}$ groups (with ≧80% monounsaturated).

Some embodiments comprise fat mimetic compounds having two short alkyl or oxaalkyl X groups. By "short" is meant having 1, 2, 3, or 4 carbon atoms. As denoted herein, where X is described as having 1, 2, 3, or 4 carbons, compositions with X groups having predominantly 1, 2, 3, or 4 carbons are included. The two short X groups may be the same or different, but compounds having two identical X groups are preferred. Example short X groups include, but are not limited to, methyl, oxamethyl, ethyl, oxaethyl, propyl, oxapropyl, butyl, and oxabutyl. As used herein, chemical names include isomeric variations; for example, "propyl" includes normal-propyl and iso-propyl.

The choice, number and arrangement of R and X groups on the siloxy ester derivatives will affect the biological as well as physical properties of the compound. Where, by virtue of any of these factors, fatty groups R are metabolized, the caloric value of the compound will increase. Preferred compounds are partially digestible and deliver 0.5 to 8.5 kcal per gram, preferably 0.5 to 6.0 kcal/gram, more narrowly 0.5 to 3.0 kcal/gram upon being metabolized.

An advantage of the present invention is that the caloric availability of siloxy ester derivatives may be modulated by the placement and selection of the R groups attached to the backbone as well as to the groups attached to silicon. For example, since long-chain saturated fatty acids are less well absorbed (Hashim, S.A., and Babayan, V.K., 31 Am. J. Clin. Nutr. S273–276 (1978)), these may be employed to decrease digestibility in some embodiments. Conversely, where an R group is metabolized, it may be a highly desirable or essential fatty acid such as linoleic acid.

Another advantage of the present invention is that, in the preferred class of compounds, the X and R groups exhibit differential reactivity on digestion. This results not only in the controlled and limited availability of effective caloric value, but also the selective conversion of the fat mimetic to a product or intermediate with a less oil-like nature. The more readily digestible fatty group can be a highly desirable essential fatty acid or a nutritionally advantageous carboxylic acid such as oleic, linoleic, linolenic, or eicosapentaenoic acids, or mixtures thereof. The more readily digestible fatty group can also comprise predominantly low molecular weight carboxylic acid species (e.g., acetic, propionic, or butyric acids) which would limit caloric delivery and provide additional ability to control functionality.

As with natural triglycerides, the more readily digestible residue can, alternatively, be a fatty acid having beneficial attributes, such as, for example, those associated with conjugated linoleic acid isomers. The product of such a controlled digestive process may be said to have decreased hydrophobicity, and correspondingly increased hydrophilicity, relative to its fat mimetic precursor. Such a product of a process of controlled digestion would tend to have not only decreased oiliness, but also increased ability to function as an emulsifier. Such a controlled digestion product will be less prone to exist in the GI tract as a persistent oil compared with substances taught in the prior art. Ideally, the enhanced emulsifying capacity of the enzymatic cleavage product derived from compositions of the invention would actually be an aid to digestion, substantially overcoming a major problem which has heretofor limited the widespread use and development of highly desirable low calorie synthetic fats and oils in foods and food preparation.

The siloxy ester derivatives of this invention may be incorporated either alone, or in combination with another fat and/or fat mimetic, into any food composition or used in conjunction with any edible material. Among fats are natural triglycerides including those rich in highly desirable or essential fatty acids, such as oleic, linoleic, linolenic, or eicosapentaenoic acid, triglycerides bearing fatty acids having beneficial attributes such as those associated with conjugated linoleic acid isomers, medium chain triglycerides and the like.

Other fat mimetics include any heretofore suggested as edible fat replacements, including, but not limited to, sugar esters (such as the sucrose polyester fat replacements disclosed, for example, in Eur. Pat. Ap. Pub. No. 236,288 to Bernhardt and U.S. Pat. No. 4,797,300 to Jandacek and Letton, the disclosures of which are incorporated herein by reference), neoalkyl esters, polyglycerol esters, malonate esters, propoxylated glycerols, retrofats, carboxy/carboxylates, polyvinyl alcohol esters and the like. Also of use in combination with the fat mimetics of this invention are the proteinaceous fat replacements disclosed in U.S. Pat. No. 4,734,287 to Yamamoto and Latella and U.S. Pat. No. 4,855,156 to Singer, et al., and carbohydrate fat replacements disclosed in U.S. Pat. No. 4,911,946 to Singer, et al., the disclosures of which are hereby incorporated by reference.

In the practice of this invention, food products comprising fat ingredients and nonfat ingredients have all or a portion of the fat ingredient replaced by the siloxy esters of this invention. When employed either alone or in food products with other fats or fat mimetics, the siloxy ester derivatives of this invention are desirably added in amounts effective to provide a significant caloric reduction of the calories due to fat. For example, a 5 to 10% or greater replacement would be effective for this purpose, and replacements of at least 20% are desired in many cases. A fat replacement of more than 20%, e.g., at least 25%, more particularly 50 to 100%, are desired in other embodiments. Replacements of one third are typical, and in many cases replacements of 75% or more are desired.

It is an advantage of this invention that the physical properties of the fat mimetics can be varied over wide ranges by judicious selection of siloxy esters and ester mixtures or components having various pendant groups. Formulations for chocolate or confectionery applications, for example, can employ groups or components yielding high-flow-temperature, sharply melting mixtures; salad oils can employ groups or components yielding low to medium-flow temperature mixtures that do not readily crystallize upon refrigeration; margarines and shortenings can employ groups or components yielding plastic mixtures; bakery products may employ groups or components stable to oxidation on storage, and so forth. By "flow temperature" is meant the temperature at which a one centimeter cube of the material, upon heating and supporting one 0.1 gram weight begins to flow. For purposes of definition, low temperatures will be within the range of up to 40° F., medium flow temperatures are within the range of from 40° to 70° F. and high flow temperatures are above 70° F., but preferably below 98° F.

The term "edible material" is broad and includes anything edible, whether or not intended for nutrition, e.g., it can be an additive such as an antioxidant for fats or oils, an antispatter agent, an emulsifier, a texture modifier such as a plasticizer for chewing gum, a component for cosmetics, or other minor functional ingredient such as a carrier or diluent for use in flavorings, pharmaceuticals, and the like.

Broadly speaking, the siloxy esters of this invention can be employed as fat replacements in fat-containing edible emulsions comprising an oil phase and an aqueous phase, including those high in fat (e.g., 75 to 85%), such as margarines and salad dressings, and those high in water (e.g., 25 to 75%), such as low fat spreads. The fat mimetics of this invention can be employed as full or partial fat substitutes in dairy, meat, nut, egg, and other food products having a high natural fat component, and in vegetable, cereal and other products having a low natural fat component. The fat mimetics of this invention can be employed as ingredients for all types of leavened baked products, both yeast raised and chemically leavened, and unleavened baked products, and as coatings or coating ingredients for the same types of products. The fat mimetics of this invention can be employed as an ingredient or a coating for snack food products, as well as a frying oil or a frying oil ingredient for fried snacks. In addition, the low calorie fat mimetics of the present invention can be employed to form edible barrier layers, either on the exposed surfaces of foods or as internal barrier layers used to separate various portions of a food product, e.g., as a barrier between a dessert filling and an outer edible shell.

Representative of fat-containing food products which can contain, in addition to other food ingredients, the siloxy esters of this invention in full or partial replacement of natural or synthetic fat are: frozen desserts, e.g., frozen novelties, ice cream, sherbet, ices, and milk shakes; salad dressings; mayonnaises and mustards; dairy and non-dairy cheese spreads; margarine, margarine substitutes and blends; flavored dips; flavored bread or biscuit spreads; filled dairy products such as filled cream and filled milk; frying fats and oils; cocoa butter replacements and blends; candy, especially fatty candies such as those containing peanut butter or chocolate; reformed and comminuted meats; meat substitutes and extenders; egg products and substitutes; nut products such as peanut butter; vegetable and fruit products;

pet foods; whipped toppings; compound coatings; coffee lighteners, liquid and dried; puddings and pie fillings; frostings and fillings; chewing gum; breakfast cereals; bakery products, e.g., cakes, breads, rolls, pastries, cookies, biscuits, and savory crackers; and mixes or ingredient premixes for any of these. The low calorie fat mimetics of this invention may also be employed in any flavor, nutrient, drug or functional additive delivery system.

Exemplary food products which can be improved by the use of the siloxy esters of this invention are: baked foods, such as cookies, crackers, biscuits, cakes and the like which all contain at least a flour or starch component in addition to the low calorie fat mimetics of this invention; snack products which are fried or coated with fat or oil and/or also contain at least a flour or starch component in addition to the low calorie fat mimetics; emulsion products, such as margarine products (e.g., full-fat, low-fat, and fat substitute products), salad dressing and mayonnaise which all contain emulsions having a fat phase including the low calorie fat mimetics and an aqueous phase; candies and confections which contain a sweetener such as sugar or aspartame in addition to the low-calorie fat mimetics; and dairy product substitutes which contain a dairy protein such as whey, casein or caseinate, or the like in addition to the low calorie fat mimetics. The margarine products also typically contain a milk component and butter flavor, while the salad dressings will contain spices and the mayonnaise, egg. Among the baked products, cakes and cookies also contain sweeteners and the crackers typically contain salt.

In one of its broad aspects, the invention provides a process for preparing a food product with reduced calories comprising adding a fat mimetic of the invention to at least one other food ingredient in the preparation of the food. The fat mimetic can be in total or partial substitution of the normal or natural fat content. Typical food ingredients will be selected from the group consisting of protein, carbohydrates, fats, nutrients, and flavors. These ingredients are typically added in the form of flours, meals, fruits, dried fruits, vegetables, dried vegetables, meats, dried meats, starches, spices, salt, dried milk solids, sugars, acidulents, buffers, emulsifiers, stabilizers, gums, hydrophilic colloids, salts, antioxidants, colors, preservatives and the like. The fat mimetic will typically be employed in an amount of at least 5%, e.g., from 10 to 90% of the composition, and one or more other food ingredients will be present at 10 to 90%. More specific ranges, appropriate for various products, are given in the Examples.

It is a further advantage of the invention that desirable physical properties can be achieved in foods containing high concentrations of naturally-occurring cis monounsaturates by blending the fat mimetics with oils rich in these, such as corn, soybean, canola, peanut, and cottonseed oils, and tallow, lard, and mixtures and fractions of these. Alternatively, it is possible to employ fatty acids or mixtures of fatty acids from fractions of one or more of these oils.

In one embodiment, the low calorie fat mimetics of this invention are mixed with natural oils such that the ratio of unsaturated to saturated residues in the resulting blend lies between 1 and 10, more narrowly between 2 and 6, and even more narrowly between 3 and 5. In one embodiment, the polyunsaturated to saturated ratio is above 10; In another, between 10 and 25. Additionally, this ratio can be increased even more by blending the fat mimetic with a highly polyunsaturated oil such as safflower, sunflower, sorghum, soybean, peanut, corn, cottonseed and sesame oils.

The following is a list of representative, but not limiting, examples of siloxy ester derivatives of this invention:

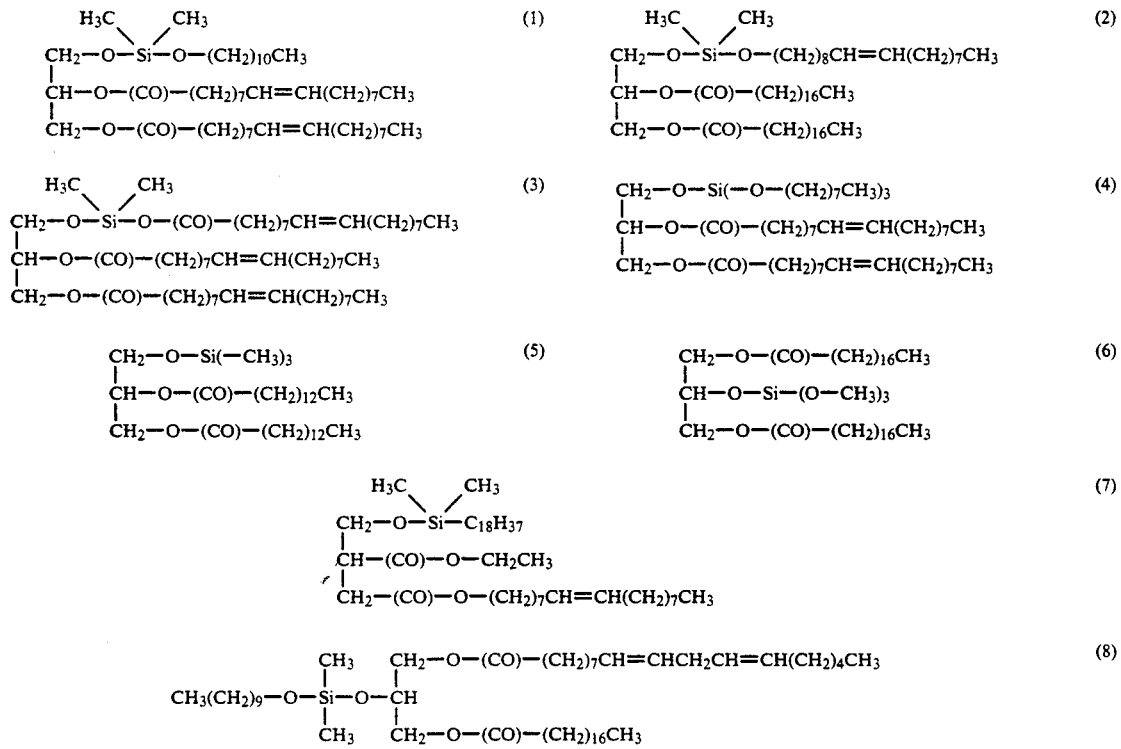

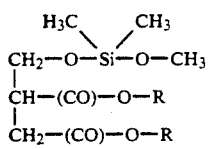 (9)

where the R groups are derived from corn oil

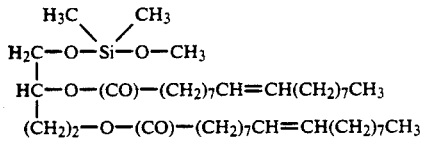 (11)

CH₂—(CO)—O—(CH₂)₇CH=CH(CH₂)₇CH₃ (13)
|
C=CH—CH₂—(CO)—O—CH₂(CH₂)₇CH=CH(CH₂)₇CH₃
|
O—Si(—CH₃)₂—C₁₈H₃₇

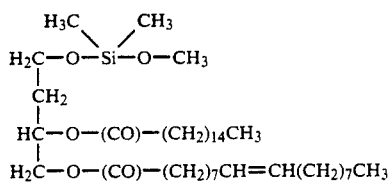 (15)

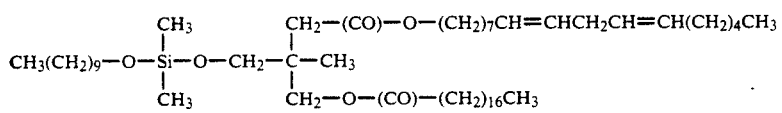 (16)

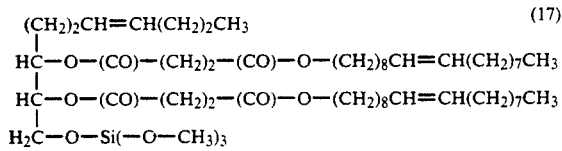 (17)

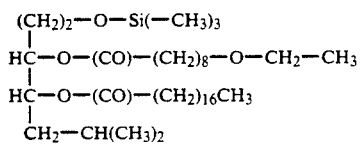 (19)

CH₂—O—Si(—O—(CO)—CH₃)₃ (10)
|
CH—O—(CO)—R
|
CH₂—O—(CO)—R where the R groups are derived from soybean oil (CH₂)₂—O—(CO)—(CH₂)₇CH=CH(CH₂)₇CH₃ (12)
|
HC—O—Si(—O—CH₃)₃
|
(CH₂)₂—O—(CO)—(CH₂)₇CH=CH(CH₂)₇CH₃

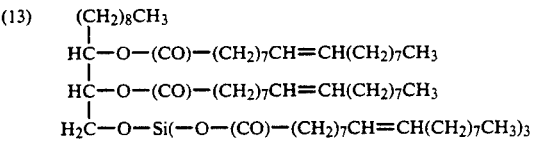 (14)

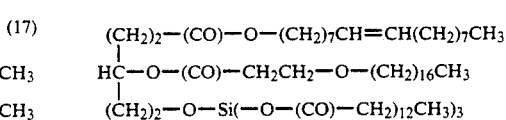 (18)

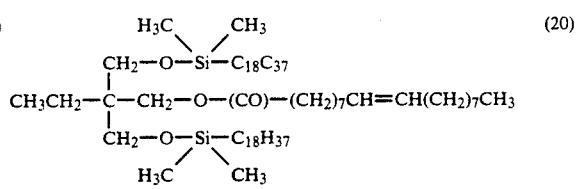 (20)

The compounds of this invention are prepared in step-wise syntheses. The silyl group or groups may be added before or after derivatization of compound hydroxyls and/or carboxylates. For example, siloxy ester fat mimetics of this invention may be prepared by the silylation of enolate anions. Alternatively, siloxy ester fat mimetics may be prepared by derivatizing alcohols or hydroxycarboxylic acids with alkyl silanes. Example syntheses are set out in the next section.

EXAMPLES

The following examples are presented to further illustrate and explain the present invention and should not be taken as limiting in any regard. Unless otherwise indicated, all parts and percentages are by weight, and are based on the weight at the particular stage of the processing being described. The proton NMR spectra have assigned chemical shifts, multiplicities, and intensities consistent with the structures with which they are reported.

EXAMPLE 1

This example illustrates how siloxy substituents may be introduced in a highly regioselective synthesis of a novel fat mimetic based on glycerol: 1-dimethyloctadecylsiloxy-2-propionyloxy-3-oleoyloxypropane, depicted in structure (7) above.

Glycidol (7.4 g, 0.1 mole), triethylamine (10.1 g., 0.1 mole) and 200 mL of tetrahydrofuran (THF) are combined in a 500-mL flask fitted with a magnetic stir bar, a reflux condenser, and an addition funnel. A solution of chlorodimethyloctadecylsilane (34.7 g, 0.1 mole) in 75 mL THF is added over 30 minutes, and the mixture is warmed to reflux for three hours. The mixture is cooled to room temperature, suction filtered, and the filtrate is placed in a clean 500-mL flask fitted as before. Lithium bromide (8.7 g, 0.1 mole) and propionic anhydride (13.0 g, 0.1 mole) are added along with sufficient THF to bring the total volume to 250 mL. This solution is heated to reflux for five hours, then is allowed to cool overnight. Cesium oleate (41.4 g, 0.1 mole) is added and the mixture is heated to reflux for eight hours. The reaction mixture is cooled to room temperature, is suction filtered, and the filtrate is evaporated by means of a vacuum rotary evaporator. The residue is dissolved in a minimum of warm hexane and is flash chromatographed through a two inch bed of silica gel, eluting with hexane. The eluate is evaporated to give the title product as a pale yellow oil.

EXAMPLE 2

In this example, a dimethyloctadecylsilyl adduct of the enol derived from dioleyl 1,3-acetone-dicarboxylate (illustrated in structure 13 above) is prepared in two steps.

Dioleyl 1,3-acetonedicarboxylate is prepared in step 1. Trichloroacetic acid (9.8 g, 0.06 mole), dimethyl 1,3-acetonedicarboxylate (139.3 g, 0.8 mole), and a 5% excess of oleyl alcohol (451.1 g, 1.68 mole) are combined in a 2000-mL flask fitted with a distillation head, thermometer, and Teflon coated stirrer bar. The system is evacuated to ~150 Torr and is heated at 130°-140° C. for 17 hours. The yield of clear orange oil is quantitative.

Proton NMR spectrum in chloroform-d: chemical shift in ppm (multiplicity, intensity, assignment): 5.35 (multiplet, 4H, HC=CH), 4.13 (triplet, 4 H, O—CH$_2$), 3.61 (singlet, 4 H, O=C—CH$_2$—C=O), 2.01, 1.62 and 1.27 (multiplets, 56 H, CH$_2$), and 0.88 (triplet, 6 H, CH$_3$). The product in CDCl$_3$ exists in keto (~68%) and enol (~32%) forms, the latter accounting for additional NMR singlets at 3.22 and 5.18 ppm (ration 2:1, respectively). These resonance lines as well as the singlet at 3.61 ppm disappear after base-catalyzed exchange of the product in excess deuterium oxide. The exchange sites are confirmed by deuterium NMR analysis.

Analysis: Calculated for C$_{41}$H$_{74}$O$_5$, formula weight 647.03: C, 76.11%; H, 11.53%; O, 12.36%. Found: C, 76.36%; H, 11.91%; O, 11.73% (by difference).

A dimethyloctadecylsilyl adduct of the enol derived from dioleyl 1,3-acetonedicarboxylate is prepared in step 2. Dioleyl 1,3-acetonedicarboxylate (12.9 g, 0.2 mole), triethylamine (20.2 g, 0.2 mole) and 200 mL THF are combined in a 500-mL flask fitted with a magnetic stir bar, a reflux condenser, and an addition funnel. A solution of chlorodimethyloctadecylsilane (69.4 g, 0.2 mole) in 150 mL THF is added over 30 minutes, and the mixture is warmed to reflux for three hours. The mixture is cooled to room temperature, suction filtered, and the filtrate is evaporated by means of a vacuum rotary evaporator. The residue is dissolved in a minimum of warm hexane and is flash chromatographed through a three-inch bed of silica gel eluting with hexane. The eluate is evaporated to give the title product as a pale yellow oil.

EXAMPLE 3

This example illustrates the derivatization of an alcohol with an alkyl silane to yield 1,3-bis(dimethyloctadecylsiloxy)-2-ethyl-2-oleoyloxymethylpropane (depicted in structure 20 above).

Trimethylolpropane (26.8 g, 0.2 mole), p-toluenesulfonic acid (0.5 g) and 200 mL acetone are combined in a 300-mL flask fitted with a reflux condenser, and the mixture is warmed to reflux for 16 hours. After cooling to room temperature, the solution is evaporated. The residue is dissolved in 200 mL methylene dichloride, and the solution is placed in a 100-mL flask fitted with a reflux condenser and a magnetic stir bar. Oleic acid (56.5 g, 0.2 mole), 4-diethylaminopyridine (1.34 g, 0.01 mole) and N,N'-dicyclohexylcarbodiimide (4.1 g, 0.2 mole) in 300 mL methylene dichloride are added, and the reaction mixture is stirred at room temperature for 24 hours. The mixture is suction filtered, and the filtrate is washed successively with 1000 mL 5% HCl, 1000 mL water, and 1000 mL 5% NaHCO$_3$ before drying over anhydrous sodium sulfate. The solution is filtered and evaporated to give an oil. This is dissolved in hexane and flash chromatographed through a two-inch bed of silica gel, eluting with hexane. The hexane eluate is evaporated to give a pale yellow oil.

A portion of the ester-ketal intermediate (~0.15 mole) is combined with 150 mL of 15% aqueous acetic acid and is warmed at 50° C. for three hours. The mixture is evaporated. The residue is dissolved in 200 mL THF and placed in a 500 mL flask fitted with a reflux condenser. Triethylamine (15 g, 0.15 mole) is added and chlorodimethyloctadecylsilane (52.1 g, 0.15 mole) in 100 mL THF is added dropwise over 20 minutes with stirring. The mixture is warmed to reflux for 5 hours and is then cooled to room temperature, filtered, and the filtrate is evaporated. The residue is dissolved in a minimum volume of warm hexane, and this solution is flash chromatographed through a two-inch bed of silica gel, eluting with hexane. Evaporation of the hexane eluate gives a colorless oil.

EXAMPLE 4

Frying Oil. A frying oil may be prepared by adding 1 ppm polydimethylsiloxane to the siloxy ester of Example 3.

EXAMPLE 5

Potato Chips. Whole peeled potatoes may be sliced, washed in water, and fried in a 1:1 mixture of Example 3 siloxy ester and peanut oil at 375° F. to desired color. The excess oil is shaken off and the chips are salted. The finished product contains about 35% fat and siloxy ester.

EXAMPLE 6

French Dressing. French dressing may be prepared by adding

|  | parts |
|---|---|
| Water | 31.09 |
| to Sugar | 15.00 |
| Salt | 2.50 |
| Spices | 2.40 |
| Xanthan Gum | 0.25 |
| Alginate | 0.14 |
| Polysorbate 60 | 0.12 | and mixing three minutes. Then

| 120 Distilled Vinegar | 12.00 |
|---|---|
| and Siloxy Ester Of Example 1 | 36.50 | are added, mixed three minutes, and homogenized at 500 psi prior to filling in the usual process.

EXAMPLE 7

Dijon Mustard. A Dijon-style mustard may be prepared by combining

| | parts |
|---|---|
| Dry White Wine | 66.1 |
| with Water | 5.0 | and bringing to a boil. To this aqueous phase is added

| | parts |
|---|---|
| Ground, Defatted Yellow Mustard Seed | 12.4 |
| Siloxy Ester of Example 2 | 6.1 |
| Honey | 6.6 |
| Onion Powder | 2.0 |
| Salt | 1.3 |
| Garlic Powder | 0.3 |
| Mustard Oleo Resin | 0.2 |

The mixture is well blended, pasteurized and packaged.

EXAMPLE 8

Peanut Butter. Peanut butter may be prepared by mixing

| Ingredient | parts |
|---|---|
| Example 1 Siloxy Ester | 35.0 |
| with Peanut Flavor | 2.0 |
| Then Corn Syrup Solids | 12.0 |
| Salt | 1.0 |
| High Fructose Corn Syrup | 10.0 | are added while agitating. When well blended,

| | parts |
|---|---|
| Defatted Peanut Flour | 40.0 | is added, and the peanut butter is mixed and packaged.

EXAMPLE 9

Imitation Sour Cream. An imitation sour cream may be prepared by adding

| | parts |
|---|---|
| Water | 75.8 |
| to Modified Starch | 2.0 |
| Avicel | 1.0 |
| Distilled Monoglyceride | 0.7 |
| and Polysorbate 60 | 0.3 | and mixing three minutes. To this is added

| | parts |
|---|---|
| Example 2 Siloxy Ester | 16.5 |
| Condensed Skim Milk | 3.5 | and the mixture mixed three minutes, cooked to 195° F., and held five minutes. This may then be cooled to 60° F., and

| | parts |
|---|---|
| Flavors and Acids | 0.2 | added, followed by filling in the usual process.

EXAMPLE 10

Soda Crackers. Soda crackers may be prepared by pre-mixing ¼ of

| | parts |
|---|---|
| Flour | 70.0 |
| Yeast | 0.2 | and sufficient water to make a dough. This is fermented for 24 hours. The remaining flour, enough water to make the total

| | parts |
|---|---|
| Water | 20.0 |
| Malt Syrup | 0.69 |
| Sodium Bicarbonate | 0.40 |
| Malt | 0.01 | are added and mixed well, the ferment added and mixed again. This is proofed for 8 hours, sheeted, and baked. Afterwards,

| | parts |
|---|---|
| Example 3 Siloxy Ester | 7.0 | is applied to the crackers, prior to packing, with

| | parts |
|---|---|
| Salt | 1.7 |

EXAMPLE 11

Fudge Base. A fudge base suitable as a milk mix (or topping) may be prepared by mixing

| Ingredient | parts |
|---|---|
| Corn Syrup | 26.0 |
| Corn Starch | 2.0 |
| Vanilla | 2.0 |
| To this are added | |
| Cocoa Powder | 25.0 |
| Siloxy Ester of Example 1 | 30.0 |
| Siloxy Ester of Example 3 | 15.0 |

The mixture is blended well and heated to pasteurizing temperature before packaging.

EXAMPLE 12

Breakfast Sausage. To make breakfast sausage, premix

| Ingredient | parts |
|---|---|
| Salt | 1.7 |
| White Pepper | 0.34 |
| Sugar | 0.18 |
| Sage | 0.17 |
| Ginger | 0.06 |
| Cardamon | 0.02 |
| Marjoram | 0.02 |
| Savory | 0.01 |
| Chop | |
| Trimmed Cali Pork Butts | 45.0 |
| Siloxy Ester of Example 2 | 35.0 |
| Ham Fat | 17.5 | with spices until blended. Grind through 3/16" plate. Package and refrigerate until use.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

We claim:

1. An edible composition comprising a fat mimetic of the formula:

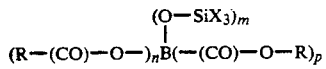

where
B is an aliphatic group having 2 to 12 carbons,
X is an alkyl or oxaalkyl having 1 to 18 carbons or an ester group of the formula —O—(CO)—R,
each R is, independently, an aliphatic group having 1 to 29 carbons,
$m = 1$ or 2,
$n = 0$ to 5, and
$p = 0$ to 5,
provided that $n + p = 1$ to 5
and one other edible ingredient.

2. A composition according to claim 1 wherein said edible composition is a food product.

3. A composition according to claim 1 wherein B has 3 to 6 carbons and $m + n + p = 3$ or 4.

4. A composition according to claim 3 wherein $m + n + p = 3$.

5. A composition according to claim 3 wherein said fat mimetic has the formula

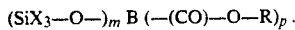

6. A composition according to claim 5 wherein $m = 1$ and $p = 2$.

7. A composition according to claim 5 wherein $m = 2$ and $p = 1$.

8. A composition according to claim 7 wherein the fat mimetics are selected from the group consisting of

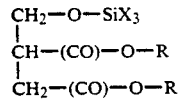

and

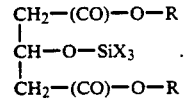

9. A composition according to claim 3 wherein said fat mimetic has the formula

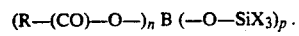

10. A composition according to claim 9 wherein $n = 1$ and $p = 2$.

11. A composition according to claim 9 wherein $n = 2$ and $p = 1$.

12. A composition according to claim 11 comprising fat mimetics selected from the group consisting of

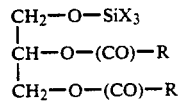

and

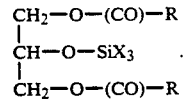

13. A composition according to claim 1 wherein $\geq 75\%$ of the R groups contain 3 to 23 carbons.

14. A composition according to claim 13 wherein 95% of said R groups contain 13 to 17 carbons.

15. A composition according to claim 1 wherein two X groups are alkyl groups.

16. A composition according to claim 15 wherein said two X alkyl groups are selected from the group consisting of methyl, ethyl, propyl and butyl groups.

17. A food composition comprising:
(a) a compound selected from the group consisting of

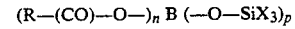

and

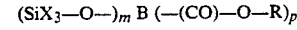

where
B is an aliphatic group having 3 to 6 carbons,
X is an alkyl or an oxaalkyl having 1 to 18 carbons, or mixtures thereof, or
an ester group of the formula —O—(CO)—R,
$m = 1$ or 2,
$n = 0$ to 2,
$p = 0$ to 2,
provided that $m + n + p = 3$ or 4, and R is an aliphatic group having 1 to 29 carbons; and
(b) at least one additional food ingredient.

18. A composition according to claim 17 wherein said food has a fat component and said compound is used in partial or full replacement of said fat component.

19. A composition according to claim 18 wherein said additional food ingredient is selected from the group consisting of flour, starch, sweeteners, salt, eggs, meat, and dairy proteins.

20. A composition according to claim 17 wherein said food composition further comprises a fat replacement selected from the group consisting of sucrose polyester and a proteinaceous fat replacement.

21. A method for preparing an edible composition having a fat ingredient comprising incorporating into said composition a compound of the formula

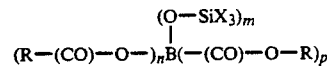

where
B is an aliphatic group having 2 to 12 carbons,
X is an alkyl or oxaalkyl having 1 to 18 carbons or an ester group of the formula —O—(CO)—R,
each R is, independently, an aliphatic group having 1 to 29 carbons,
$m = 1$ or 2, n=0 to 5, and
p=0 to 5,
provided that n+p=1 to 5, in full or partial replacement of said fat component.

22. A method according to claim 21 wherein said fat ingredient is at least 25% replaced by said compound.

23. A method according to claim 21 wherein incorporating said compound reduces the calories in said edible composition.

24. A method according to claim 21 wherein said compound delivers 0.5 to 6 kcal/gram upon being metabolized.

25. A method according to claim 21 wherein B has 3 to 6 carbons, m+n+p=3 or 4, and ≧75% of said R groups have 3 to 23 carbons.

26. A method according to claim 25 wherein said compound has two $C_1$ to $C_4$ alkyl or oxaalkyl X groups.

* * * * *